United States Patent
Sonderegger

(10) Patent No.: US 10,946,138 B2
(45) Date of Patent: Mar. 16, 2021

(54) SUBCUTANEOUS INFUSION SET WITH SIDE PORT FLUID CONNECTOR

(71) Applicant: Becton, Dickinson and Company, Franklin Lakes, NJ (US)

(72) Inventor: Ralph L. Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 79 days.

(21) Appl. No.: 16/245,797

(22) Filed: Jan. 11, 2019

(65) Prior Publication Data

US 2019/0143032 A1   May 16, 2019

Related U.S. Application Data

(62) Division of application No. 13/943,365, filed on Jul. 16, 2013, now Pat. No. 10,220,137.

(Continued)

(51) Int. Cl.
*A61M 5/162* (2006.01)
*A61M 39/02* (2006.01)
*A61M 5/158* (2006.01)

(52) U.S. Cl.
CPC ........... *A61M 5/162* (2013.01); *A61M 5/158* (2013.01); *A61M 39/0247* (2013.01); *A61M 2005/1585* (2013.01); *A61M 2005/1586* (2013.01); *A61M 2005/1587* (2013.01); *A61M 2039/027* (2013.01); *A61M 2039/0258* (2013.01)

(58) Field of Classification Search
CPC .......... A61M 5/162; A61M 2005/1585; A61M 2005/1586; A61M 2005/1587; A61M 2039/0258; A61M 2039/027; A61M 39/0247; A61M 5/158
See application file for complete search history.

(56) References Cited

U.S. PATENT DOCUMENTS

| 4,755,173 A | 7/1988 | Konopka et al. |
| 6,506,181 B2 | 1/2003 | Meng et al. |

(Continued)

FOREIGN PATENT DOCUMENTS

| JP | S62201159 A | 9/1987 |
| JP | 2007510498 A | 4/2007 |

(Continued)

OTHER PUBLICATIONS

Extended European Search Report dated Dec. 13, 2013 issued by the European Patent Office in counterpart EP Application No. 13177631.2.

*Primary Examiner* — Jason E Flick
(74) *Attorney, Agent, or Firm* — Dickinson Wright PLLC

(57) ABSTRACT

A method of coupling an extension set hub comprising a blunt cannula, with an infusion set comprising a base, an upper septum, a lower septum, and a septum cap enclosing said upper and lower septa, said septum cap comprising at least one radial port and at least one axial port, the method comprising the steps of affixing said base to a skin surface of a user, moving said extension set hub in a direction substantially parallel to said base until said blunt cannula passes through said radial port and between said upper septum and said lower septum within said septum cap, and rotating said extension set hub about said base until reaching a desired position.

11 Claims, 6 Drawing Sheets

Related U.S. Application Data

(60) Provisional application No. 61/677,829, filed on Jul. 31, 2012.

(56) References Cited

U.S. PATENT DOCUMENTS

| | | |
|---|---|---|
| 6,719,726 B2 | 4/2004 | Meng et al. |
| 7,670,317 B2 | 3/2010 | Cindrich et al. |
| 7,699,808 B2 | 4/2010 | Marrs et al. |
| 7,731,691 B2 | 6/2010 | Cote et al. |
| 7,985,199 B2 | 7/2011 | Kornerup et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2008/0103450 A1* | 5/2008 | Marrs .................. A61M 5/158 604/174 |
| 2009/0069750 A1 | 3/2009 | Schraga |
| 2009/0143763 A1 | 6/2009 | Wyss et al. |
| 2011/0288482 A1 | 11/2011 | Farrell et al. |
| 2011/0301541 A1 | 12/2011 | White et al. |

FOREIGN PATENT DOCUMENTS

| | | |
|---|---|---|
| JP | 2009069750 A | 4/2009 |
| JP | 2010051702 A | 3/2010 |
| JP | 2011520507 A | 7/2011 |
| WO | 2009139857 A1 | 11/2009 |

* cited by examiner

SUBCUTANEOUS INFUSION SET WITH SIDE PORT FLUID CONNECTOR

CROSS-REFERENCE TO RELATED APPLICATIONS

This application is a division of U.S. Nonprovisional application Ser. No. 13/943,365, filed Jul. 16, 2013, which claims the benefit under 35 U.S.C. § 119(e) of U.S. Provisional Application Ser. No. 61/677,829, filed on Jul. 31, 2012, the entire contents of both of said prior applications being incorporated herein by reference.

FIELD OF THE INVENTION

The present invention relates generally to a subcutaneous infusion set having a side port fluid connector. The infusion set can be inserted and attached to the skin using commercially available inserter devices.

BACKGROUND OF THE INVENTION

One mode of insulin infusion treatment includes infusion pump therapy provided via a catheter, needle or other type of cannula incorporated into an infusion set. Infusion pumps offer the advantages of controllable and/or continuous infusion of insulin, precision dosing, and programmable delivery schedules as desired by the user or required by the application. Together, these advantages result in a number of benefits, such as more accurate blood glucose control. In this mode of insulin infusion treatment, the infusion pump remains attached to the user and the required doses of insulin are delivered to the user via the catheter, needle or other type of cannula incorporated into the infusion set.

One type of cannula incorporated into an infusion set for performing such treatments is a catheter, which generally is a flexible tube that can be inserted into the body to permit the administration of fluids to a targeted location. In infusion pump therapy, the types and sizes of the catheter may vary, but generally, the catheter is a thin, flexible tube with one or more openings to permit fluid communication. In some uses, however, the catheter can comprise a larger diameter and/or length, and can be constructed of rigid material or a combination of rigid and flexible materials.

One type of conventional infusion set is sold as the Quick-Set @ infusion set manufactured by Medtronic. In this device, a catheter assembly is provided which is connected to an infusion pump via a tube set, and an insertion device is used to insert or attach the catheter assembly to a user. The infusion set and insertion device can also be combined or integrated, as in the Mio® infusion set manufactured by Medtronic, which is an "all-in-one" design that combines the infusion set and insertion device into a single unit.

Catheter infusion sets are often complex in design and do not provide a quick or simple method for fully priming the infusion set prior to subcutaneous injection of medicaments. Further, catheter infusion sets are often bulky and indiscreet when used under the clothing of a user. Catheter infusion sets can also be uncomfortable due to the torque placed upon the needle injection site from a rigid placement of the infusion set and tubing in relation to the infusion pump.

Accordingly, a need exists for an improved infusion set design and construction that will reduce construction costs and provide for mobility and comfort for the user while allowing discreet wearability of the infusion set and pump.

SUMMARY OF THE INVENTION

An object of the present invention is to substantially address the above and other concerns, and provide an infusion set that is simple to manufacture, by using fewer components and materials, that will reduce construction costs, and that will provide for mobility and comfort for the user while allowing discreet wearability of the infusion set and pump.

Another object of the present invention is to provide an infusion set that can be primed prior to subcutaneous or intradermal injection of medicaments.

Another object of the present invention is to provide an infusion set that provides greater mobility for a user though a side port extension set that rotates up to 360 degrees around the injection site.

Another object of the present invention is to provide an infusion set that incorporates a multiple septum design and/or multiple septa for incorporation with such an infusion set.

Another object of the present invention is to provide an infusion set with a thin and/or rounded profile that allows the infusion set to be small and unobtrusive and which places the infusion set closer to the skin, and thus results in an infusion set that is more discreet when worn by a user.

These and other objects are substantially achieved by providing an exemplary infusion set that includes upper and lower septa within a base that can be surrounded by a septum cap with a plurality of access ports. A blunt cannula can be included with an extension set hub and can be configured to fit through one of the access ports of the septum cap and penetrate the interface between the upper septum and the lower septum to provide fluid communication from an infusion pump to the infusion set. However, to reduce the number of components in the device, the upper septum and the lower septum can be combined and/or replaced with a single septum. The septum cap can be rotatable on the base permitting the blunt cannula of the extension set to slide between the interface between the upper septum and the lower septum in a 360 degree manner along with the extension set hub as the septum cap is turned in a 360 degree manner.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 1:
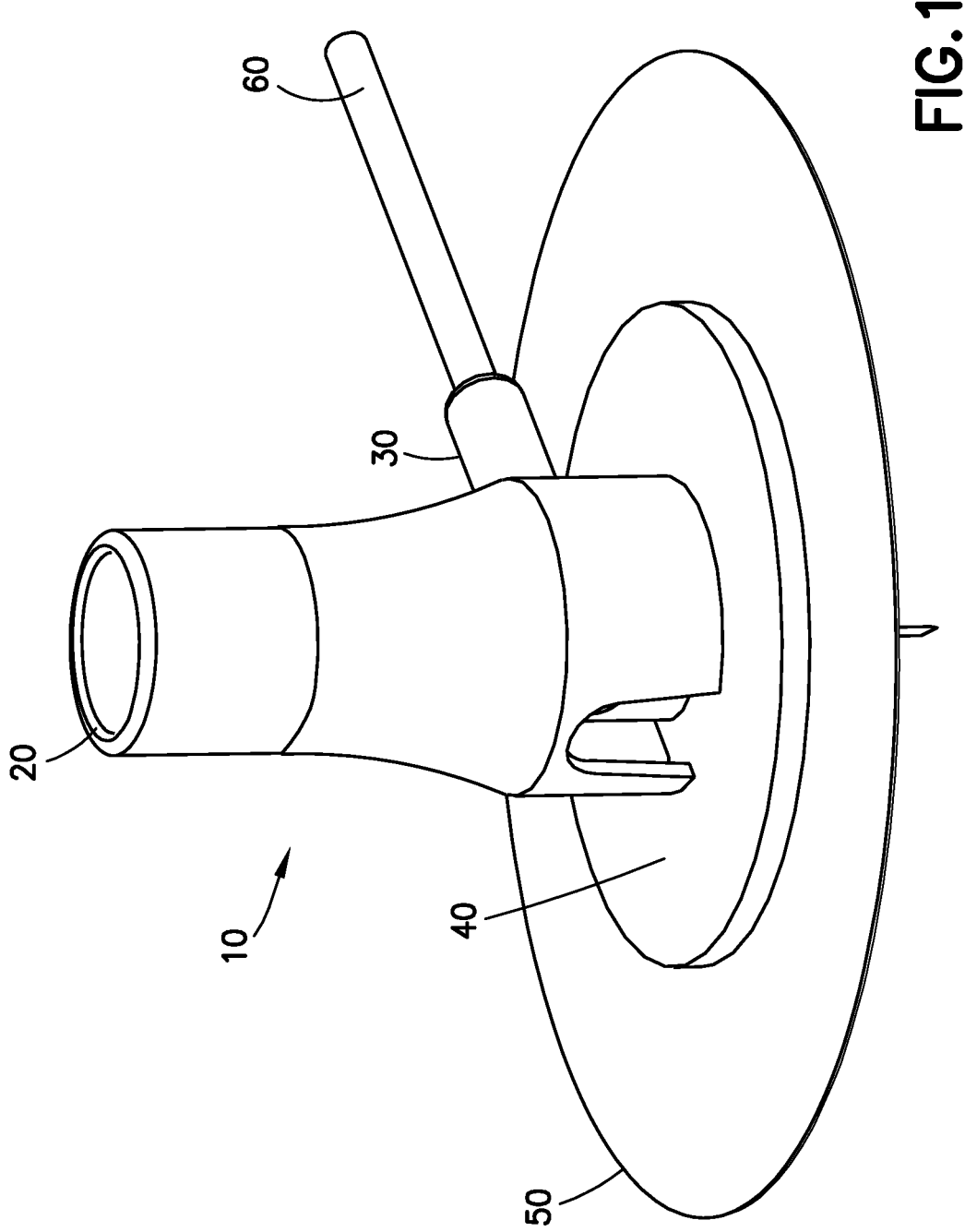
FIG. 1 is an enlarged perspective view of an infusion set configured for placement on a user and with an extension set tubing hub (i.e., fluid connector) attached in accordance with an embodiment of the present invention.

As will be appreciated by one skilled in the art, there are numerous ways of carrying out the examples, improvements and arrangements of the infusion devices disclosed herein. Although reference will be made to the exemplary embodiments depicted in the drawings and the following descriptions, the embodiments disclosed herein are not meant to be exhaustive of the various alternative designs and embodiments that are encompassed by the disclosed invention. The following description is provided in regard to a subcutaneous application of the invention, but embodiments are not limited thereto. Exemplary embodiments of the present invention can be applied equally to intradermal, intramuscular and subcutaneous applications.

An exemplary infusion device of the present invention is illustrated in FIGS. 1-5. The device is a subcutaneous infusion set that can be attached to a patient's skin surface using an inserter or needle hub, and connected to an infusion pump (not shown), for the delivery of insulin or other medicament to the patient. An exemplary subcutaneous infusion set is shown with an inserter needle hub, but can be used with existing inserters, such as the Medtronic Quick-Serter®, with little or no modification. FIGS. 1-5 illustrate a configuration wherein a subcutaneous infusion set can be primed for placement on a user, either manually or with the aid of a commercially available or custom-designed inserter device.

Figure 2:
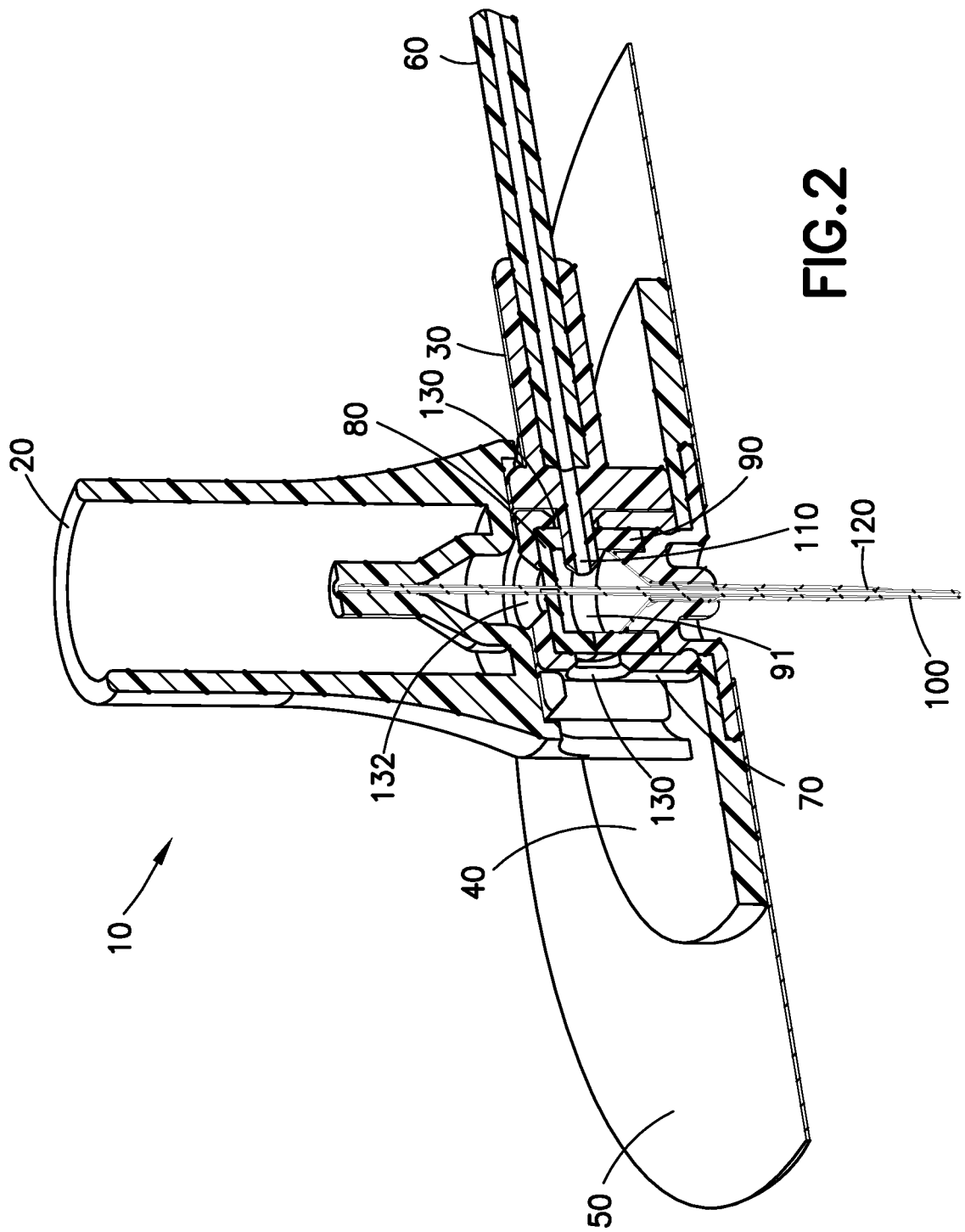
FIG. 2 is an enlarged cross-sectional view of the infusion set of FIG. 1 with the extension set tubing hub attached in accordance with an embodiment of the present invention.

FIG. 1 is an enlarged perspective view of an infusion set configured for placement on a user and with an extension set tubing hub (i.e., fluid connector) attached in accordance with an embodiment of the present invention, and FIG. 2 is an enlarged cross-sectional view of the infusion set of FIG. 1.

As shown in FIGS. 1 and 2, the exemplary device 10 comprises a needle hub 20 aligned above and removably coupled with an extension set hub 30. The extension set hub 30 is aligned above and removably coupled with a base 40. A skin adhesive layer 50 is disposed upon a lower, skin-contacting surface of the base 40, and is configured to be attachable to the skin of a user. The extension set hub 30 comprises flexible extension set tubing 60 to provide medicament communication between the extension set hub 30 and an infusion pump (not shown). A connector (not shown) of the extension set tubing 60 connects to the infusion pump so that medication from the pump, such as insulin, can be delivered to the extension set hub 30.

Figure 3:
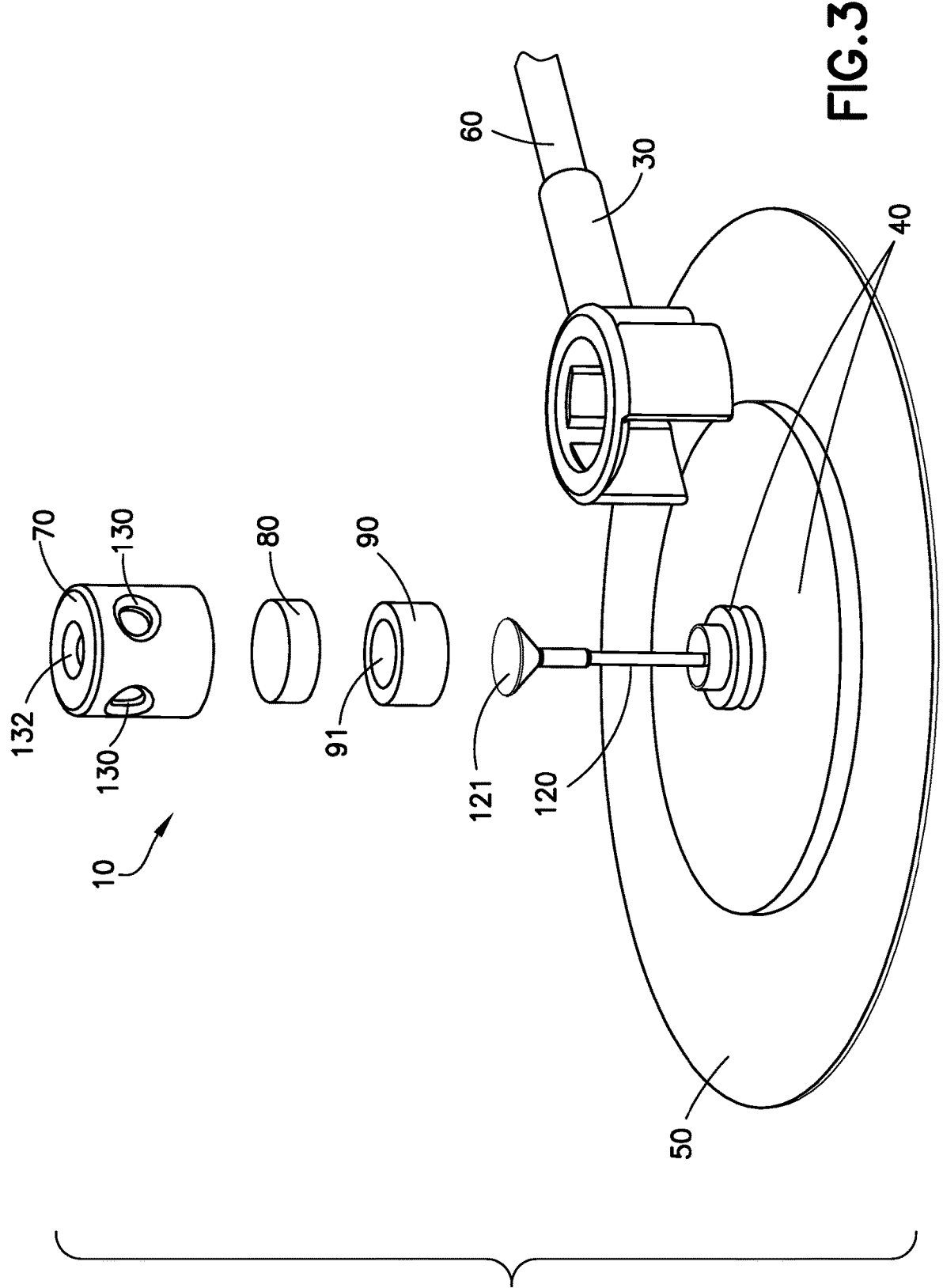
FIG. 3 is an enlarged exploded view of the infusion set of FIG. 1 illustrating its individual components including those of the extension set tubing hub in accordance with an embodiment of the present invention.

As shown in greater detail in FIGS. 2 and 3, the exemplary device 10 further comprises a rigid septum cap 70 that encapsulates at least an upper resilient septum 80, a lower resilient septum 90, and a catheter 120. For illustration purposes, a flexible, plastic catheter 120 is discussed, and is provided in communication with the septa in a flared manner using a wedge for example, such as a metal wedge 121. The septum cap 70 is aligned above and rotatably coupled to the upper septum 80, which in turn is aligned above and pressed against the lower septum 90. The lower septum 90 is aligned above and pressed against the catheter 120 and wedge 121.

As shown in FIGS. 2 and 3, the lower septum 90 is generally in the form of a hollow cylinder and includes a chamber 91 within. In one exemplary embodiment, the lower septum 90 is configured to receive a blunt cannula through one of a plurality of openings. The upper septum 80 may be solid and generally disk-shaped, or it may be in the form of an inverted cylindrical cup, preferably having a diameter substantially equal to the diameter of the lower septum 90. When pressed against the lower septum 90, the upper septum 80 forms a pierceable, sealed top of the chamber 91. In one exemplary embodiment, the upper septum 80 is configured to receive a sharp cannula and self-seal the opening created by the sharp cannula when the cannula is removed, but is not limited thereto. For example, in another exemplary embodiment, the upper septum 80 is pre-slit and configured to receive a sharp or blunt cannula and self-seal the opening created by the cannula when the cannula is removed. The bottom of the chamber 91 is formed by the catheter 120 and wedge 121, thereby creating a fluid communication path between the chamber 91 and any openings at a proximal end of the catheter 120.

Further, when the upper septum 80 is pressed against the lower septum 90, a fluid seal is created at the annular area of contact between septa 80 and 90. However, as described in greater detail below, a blunt cannula of the extension set hub 30 can be inserted between the septa 80, 90 and can be rotated up to 360 degrees around the seal created at the area of contact between septa 80 and 90. The septum cap 70 includes at least one radial access port 130 configured to receive a blunt cannula of the extension set hub 30 in a motion parallel to the skin surface, and an axial access port 132 configured to receive an insertion needle in a motion perpendicular to the skin surface. Any of the above features can be molded as a single shot or as a rigid single shot and a flexible second shot.

Returning to FIG. 2, the needle hub 20 comprises a sharp introducer needle 100 for insertion of the catheter 120. The upper septum 80 is configured to be pierced on its upper surface by the sharp introducer needle 100, which is hollow and anchored in the needle hub 20, through the access port 132 of the septum cap 70. After the base 40 and catheter 120 have been attached to a skin surface of the user, the sharp introducer needle 100 is removed by manually withdrawing the needle hub 20 from the catheter 120. When the needle hub 20, to which the sharp introducer needle 100 is attached, is removed, the sharp introducer needle 100, which is secured to the needle hub 20, is pulled through the upper surface of the upper septum 80 and septum cap 70. When the sharp introducer needle 100 is pulled free of the upper septum 80, the upper septum 80 self-closes the opening through which the sharp introducer needle 100 has been removed and thereby seals the chamber 91 created by the upper septum 80 and lower septum 90.

Figure 4:
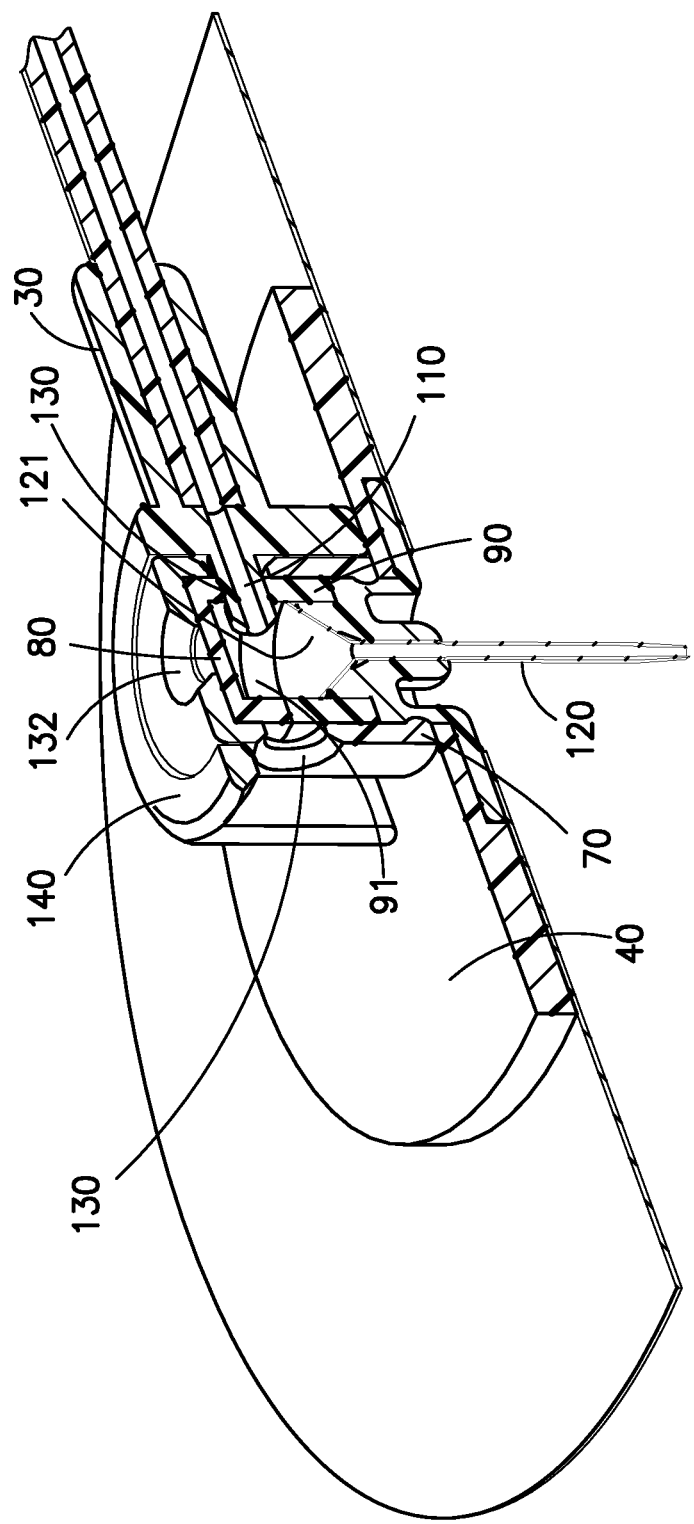
FIG. 4 is an enlarged cross-sectional view of the infusion set of FIG. 1 wherein the extension set tubing hub is engaged with the septum cap and illustrating a blunt cannula of the extension set tubing hub penetrating an interface between the upper and lower septa in accordance with an embodiment of the present invention.
Figure 5:
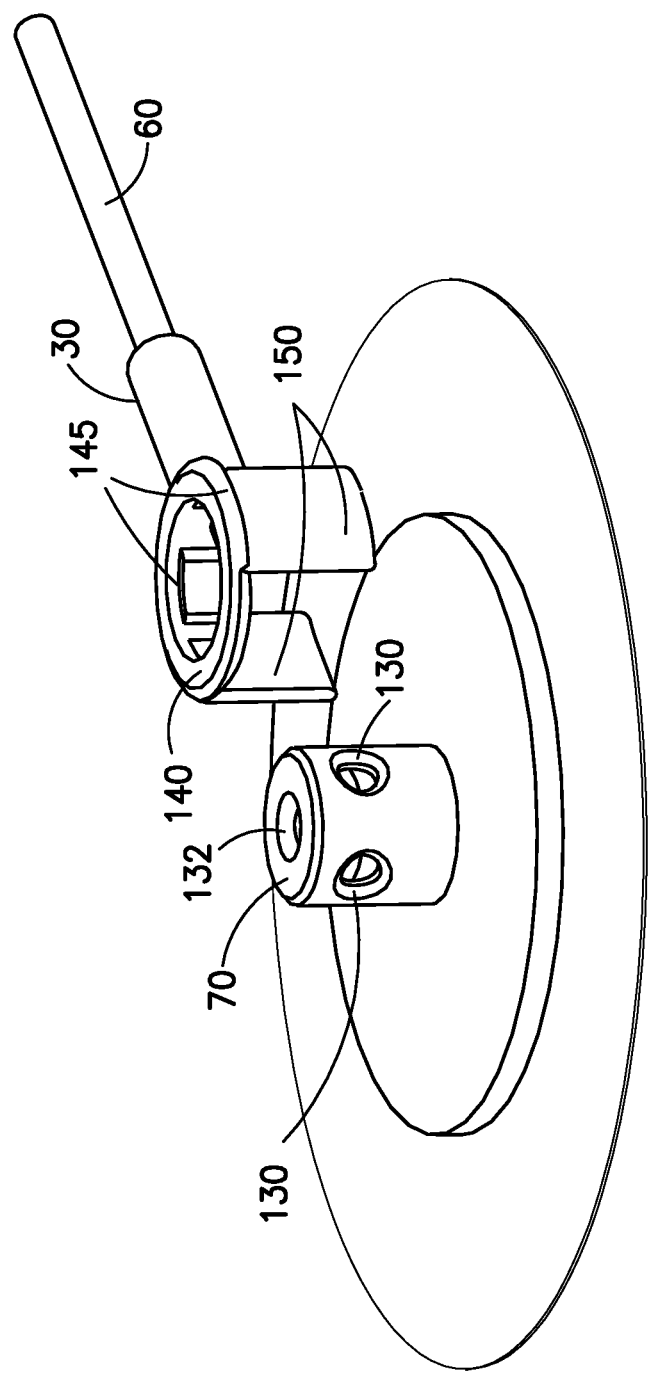
FIG. 5 is an enlarged perspective view of the infusion set of FIG. 1 prior to engaging the extension set tubing hub with the septum cap in accordance with an embodiment of the present invention.

Referring to FIGS. 4 and 5, the extension set hub 30 includes a snap ring 140 and guidance feature 150 comprising one or more ring-shaped walls protruding vertically from the snap ring 140. The extension set hub 30 further includes a blunt cannula 110 molded, formed, glued or otherwise secured and extending from one or more of the ring-shaped walls, but is not limited thereto. For example, in another exemplary embodiment, the extension set hub can include a sharpened cannula. For illustration purposes, a blunt cannula 110 is discussed. The guidance feature 150 aids in aligning the blunt cannula 110 of the extension set hub 30 for insertion within one of the access ports 130 of the septum cap 70. Molded-in, cut or otherwise provided hinges 145 of the snap ring 140 are configured to flex to allow ring-shaped walls of the snap ring 140 to deflect around the septum cap 70 during insertion of the blunt cannula 110 according to an exemplary embodiment of the present invention. This allows for a snap-fit engagement between the ring-shaped walls of the snap ring 140 and the septum cap 70.

Referring again to FIG. 4, the septum cap 70 includes at least one radial access port 130 configured to receive the blunt cannula 110 of the extension set hub 30 in a motion parallel to the skin surface, and an axial access port 132 configured to receive an introducer needle in a motion perpendicular to the skin surface. The blunt cannula 110 fits within one of the access ports 130 and penetrates the interface between the upper septum 80 and the lower septum 90, which allows the user to receive medication from the infusion pump via a fluid path created from the infusion pump, through the extension set tubing 60, the extension set hub 30, the chamber 91 of the lower septum 90 and into the catheter 120. As noted above, the upper septum 80 self-closes the opening through which the sharp introducer needle 100 of the needle hub 20 has been removed. The fluid path created by the penetration of the blunt cannula 110 between the upper septum 80 and the lower septum 90 remains after the removal of the needle hub 20 and the sharp introducer needle 100 is pulled free of the upper septum 80.

As shown in FIGS. 4 and 5, the snap ring 140 of the extension set hub 130 engages the septum cap 70 in a snap-fit manner and to maintain the extension set hub 30 in place with relation to the base 40 and the catheter 120. In this and other exemplary embodiments of the present invention, the septum cap 70 can be rotatable on the base 40, but is not limited thereto. For example, in another exemplary embodiment, the septum cap can become fixed upon installation with the base 40. For illustration purposes, a septum cap 70 that is rotatable on the base 40 is discussed. As a result, once the snap ring 140 of the extension set hub 30 is engaged with the septum cap 70, both the extension set hub 30 and the septum cap 70 are allowed to rotate 360 degrees around their respective axes on the base 40. Because the blunt cannula 110 of the extension set hub 30 penetrates the interface between the upper septum 80 and the lower septum 90, and does not pierce or attach to either septum, it can slide along the interface between the upper septum 80 and the lower septum 90 in a 360 degree manner along with the extension set hub 30. Therefore, the subcutaneous infusion set 10 is freely rotatable when the catheter 120 is introduced into a subcutaneous layer of the skin of a patient.

FIG. 5 illustrates a method of alignment and installation (or removal) of the extension set hub 30 with the septum cap 70 and the base 40. As noted above, the extension set hub 30 includes a guidance feature 150 comprising one or more ring-shaped walls protruding vertically from the snap ring 140. The guidance feature 150 aids in aligning the blunt cannula 110 of the extension set hub 30 for insertion within one of the access ports 130 of the septum cap 70 using a motion substantially parallel to a skin surface. Flexible materials, cuts, detents, or molded hinges 145 of the snap ring 140 flex to allow enough movement of the ring-shaped walls of the snap ring 140 to deflect around the cylindrical septum cap 70 during insertion of the blunt cannula 110 according to an exemplary embodiment of the present invention. Once in position, the ring-shaped walls of the snap ring 140 form a snap-fit engagement between the snap ring 140 of the extension set hub 30 with the septum cap 70 and the base 40. Removal of the extension set hub 30 from the septum cap 70 and the base 40 is performed by using an opposite motion substantially parallel to a skin surface.

Once in position, the infusion set provides a rotatable connection to the infusion pump to thereby simplify the positioning of the infusion set, tubing and pump during use. Further, as the coupling and de-coupling movements of the extension set hub are performed using a motion substantially parallel to a skin surface, the placement of the infusion set is not affected and greater user comfort is provided. Still further, by using the interface between the upper septum and the lower septum as the access point for the blunt cannula, movement of the extension set hub in a 360 degree manner is permitted. However, to still further reduce the number of components in the device, the upper septum and the lower septum can be combined and/or replaced with a single septum.

Figure 6:
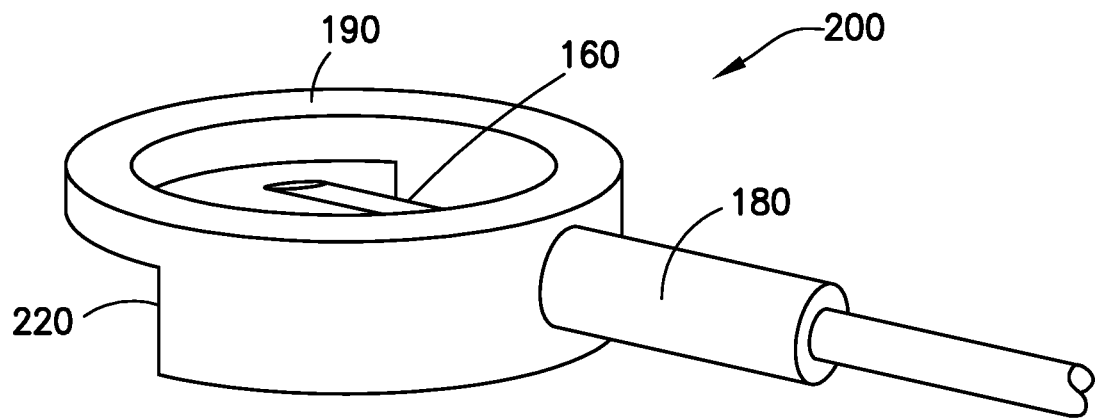
FIG. 6 is an enlarged perspective view of another embodiment of an infusion set including a single septum and a sharp cannula with an extension set tubing hub in accordance with an embodiment of the present invention.
Figure 7:
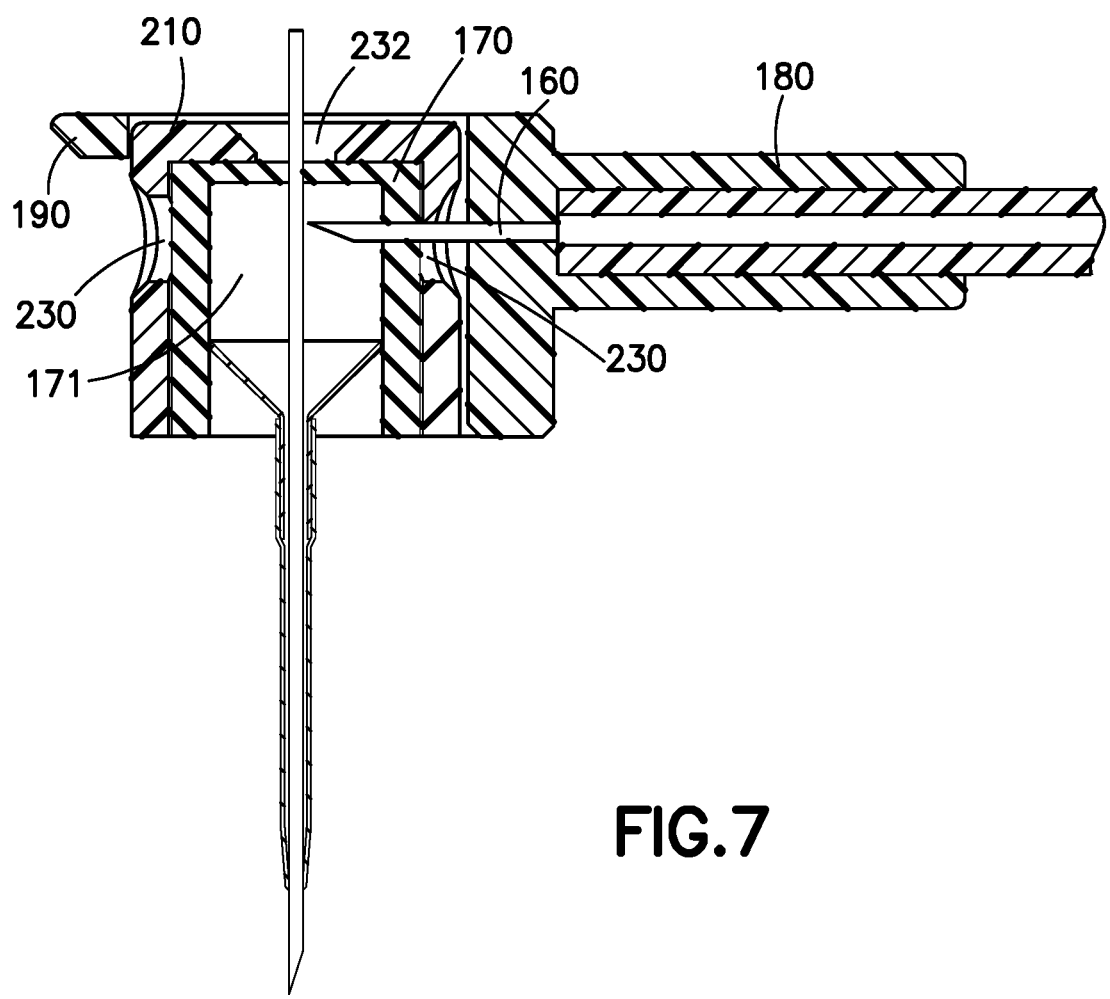
FIG. 7 is an enlarged cross-sectional view of the infusion set of FIG. 6 illustrating an exemplary relationship between an introducer needle, the sharp cannula of the extension set tubing hub, and the single septum, in accordance with an embodiment of the present invention.

For example, FIGS. 6 and 7 are enlarged views of another embodiment of an infusion set including a single septum and a sharp cannula with an extension set tubing hub in accordance with an embodiment of the present invention. The exemplary device 200 of FIGS. 6 and 7 is substantially the same as device 10 described above. However, the device 200 comprises a single septum 170 contained within a septum cap 210 having at least one radial access port 230 and an axial port 232. In one exemplary embodiment, the single septum 170 is configured to receive a sharp cannula through either of a side and a top surface, and self-seal the opening created by the sharp cannula when the cannula is removed. The device 200 further comprises an extension set hub 180 having a sharp cannula 160 configured to enter the septum cap 210 as described above and pierce a side wall of the single septum 170 as illustrated in FIG. 7.

The extension set hub 180 includes a ring-shaped guidance feature wall 220 protruding vertically from a snap ring 190. Similar to other embodiments of the present invention, the guidance feature wall 220 aids in aligning the sharp cannula 160 of the extension set hub 180 for insertion within one of the access ports 230 and to pierce a side wall of the single septum 170. This allows the user to receive medication from the infusion pump via a fluid path created from the infusion pump, through the extension set tubing, the extension set hub 180, the chamber 171 of the septum 170 and into the catheter. The septum 170 is configured to self-close the opening through which the sharp introducer needle 100 of the needle hub 20 has been removed, and the fluid path created by the penetration of the sharp cannula 160 through the septum 170 remains after the removal of the needle hub 20 and the sharp cannula needle 100 is pulled free of the septum 170.

The snap ring 190 flexes to allow enough deflection for the snap ring 190 to deflect around the septum cap 210 during insertion of the sharp cannula 160. This allows for a snap-fit engagement between the snap ring 190 and the septum cap 210. Molded-in, cut or otherwise provided hinges of the snap ring 190 are configured to flex to allow the snap ring 190 ring-shaped walls 220 to deflect around the septum cap during insertion of the sharp cannula 160 through the septum 170 according to an exemplary embodiment of the present invention. This allows for a snap-fit engagement between the snap ring 190 ring-shaped walls and the septum cap 70.

Once in position, coupling and de-coupling of the extension set hub and tubing is performed using a motion substantially parallel to the skin surface and at a user-selectable rotational position, such that the placement of the infusion set is not affected and greater user comfort is provided.

Further, the extension set hub and tubing can be easily primed before coupling with the septum cap and base. For example, before attaching the extension set hub 30 with the septum cap 70 as shown in FIG. 5, the user can activate the infusion pump or reservoir (not shown) to communicate medicament up to the blunt cannula 110. The user can then easily couple the primed extension set hub 30 and tubing using a motion substantially parallel to the skin surface and at a user-selectable rotational position. In a similar manner, before attaching the extension set hub 180 with the septum cap 210 as shown in FIG. 7, the user can activate the infusion pump or reservoir (not shown) to communicate medicament up to the sharp cannula 160. The user can then easily couple the primed extension set hub 180 and tubing using a motion substantially parallel to the skin surface and at a user-selectable rotational position.

The needle hub, extension set hub, base and septum cap of each embodiment can be constructed of materials having a rigid, moldable property, such as thermoplastic elastomer (TPE), thermoplastic urethane (TPU) or similar material. In an exemplary embodiment, the base can be molded as a single shot, or as a rigid first shot and a flexible second shot. The upper, lower and single septa of each embodiment can be constructed of materials having a viscoelastic property, such as silicone.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A method of coupling an extension set hub comprising a blunt cannula, with an infusion set comprising a base, an upper septum, a lower septum, an interface between said upper and lower septa, and a septum cap enclosing said upper and lower septa, said septum cap comprising at least one radial port and at least one axial port, the method comprising the steps of:
    affixing said base to a skin surface of a user;
    moving said extension set hub in a direction substantially parallel to said base until said blunt cannula passes through said radial port and between said upper septum and said lower septum within said septum cap; and
    rotating said extension set hub freely around said interface until reaching a desired position.

2. The method of claim 1, wherein said extension set hub comprises:
    a snap-ring comprising a substantially circular ring; and
    a plurality of guidance walls extending therefrom.

3. The method of claim 2, further comprising releasably securing said plurality of guidance walls to an outer circumference of said septum cap.

4. The method of claim 2, further comprising guiding, via said plurality of guidance walls, said blunt cannula through said radial port and into said interface.

5. The method of claim 2, further comprising flexing the snap-ring to deflect around and engage the septum cap.

6. The method of claim 2, further comprising flexing the snap-ring to expand around and disengage the septum cap.

7. The method of claim 1, further comprising rotatably sliding said blunt cannula into said interface.

8. The method of claim 1, further comprising rotatably coupling said septum cap with said base.

9. The method of claim 1, further comprising removing said blunt cannula from said radial port.

10. The method of claim 9, further comprising self-closing an opening in said interface when said blunt cannula is removed.

11. The method of claim 1, further comprising rotating said extension set hub freely up to 360 degrees about said interface of said base to reach the desired position.

* * * * *